United States Patent [19]

Goe et al.

[11] Patent Number: 5,218,122

[45] Date of Patent: Jun. 8, 1993

[54] PYRIDINE BASE SYNTHESIS PROCESS AND CATALYST FOR SAME

[75] Inventors: Gerald I. Goe, Greenwood; Robert D. Davis, Indianapolis, both of Ind.

[73] Assignee: Reilly Industries, Inc., Indianapolis, Ind.

[21] Appl. No.: 555,804

[22] Filed: Jul. 18, 1990

Related U.S. Application Data

[63] Continuation of Ser. No. 252,808, Sep. 30, 1988, abandoned.

[51] Int. Cl.$^5$ .................. C07D 213/10; C07D 213/12
[52] U.S. Cl. ..................................... 546/251; 546/250; 546/253
[58] Field of Search ........................ 546/250, 251, 253

[56] References Cited

U.S. PATENT DOCUMENTS

| | | | |
|---|---|---|---|
| 2,744,904 | 5/1956 | Cislak et al. | 546/253 |
| 2,807,618 | 9/1957 | Cislak et al. | 546/253 |
| 4,220,783 | 9/1980 | Chang et al. | 546/251 |
| 4,675,410 | 6/1987 | Feitler et al. | 546/251 |

FOREIGN PATENT DOCUMENTS

| | | | |
|---|---|---|---|
| 0851727 | 9/1970 | Canada | 546/251 |
| 0852745 | 9/1970 | Canada | 546/251 |
| 1255661 | 6/1957 | Fed. Rep. of Germany | 546/251 |
| 1903878 | 9/1969 | Fed. Rep. of Germany | 546/251 |
| 2203384 | 8/1973 | Fed. Rep. of Germany | 546/251 |
| 1188891 | 4/1970 | United Kingdom | 546/251 |
| 1235390 | 6/1971 | United Kingdom | 546/251 |

OTHER PUBLICATIONS

E. G. Derouane, "New Aspects of Molecular Shape-Selectivity: Catalysis by Zeoliet ZSM-5," *Catalysis by Zeolites,* ed. B. Imelik, et al., Elsevier, Amsterdam, pp. 5–18 (1980).

Beschke, *Ullmann Encyclopedia,* p. 593 (1980).

*Primary Examiner*—Alan L. Rotman
*Attorney, Agent, or Firm*—Woodard, Emhardt, Naughton, Moriarty & McNett

[57] ABSTRACT

An improved base synthesis process and catalyst for the preparation of pyridine or its alkylpyridine derivatives involving the catalytic reaction of one or more aldehydes and/or ketones containing from one to about five carbon atoms, with at least one reactant having more than one carbon atom, with ammonia in the gas phase. The improved catalyst comprises an effective amount of a shape-selective zeolite which has been modified by treatment with one or more metal ions or compounds of tungsten. zinc or tin. The preferred zeolite has a constraint index of about 1 to 12 and a high silica content and correspondingly low concentration of ion-exchange sites with minimal to no acidic sites present.

15 Claims, No Drawings

PYRIDINE BASE SYNTHESIS PROCESS AND CATALYST FOR SAME

This application is a continuation of application Ser. No. 252,808, filed Sep. 30, 1988.

BACKGROUND OF THE INVENTION

This invention relates to an improved process for pyridine base synthesis, and to a particular class of shape-selective zeolite catalysts for use in the same which have been advantageously modified by treatment with one or more compounds containing tungsten, zinc or tin.

The term "base synthesis" is known and used in the pyridine field and in this application to identify a process by which bases of pyridine or alkylpyridine derivatives are prepared by reacting aldehydes and/or ketones with ammonia in the gas phase using a heterogeneous catalyst. Some examples of base synthesis reactions (and their common names where appropriate) include: the synthesis of pyridine and beta-picoline from acetaldehyde and formaldehyde (the "pyridine-beta reaction"); the synthesis of alpha- and gamma-picoline from acetaldehyde (the "alpha-gamma reaction"); the synthesis of 2,6-dimethylpyridine ("2,6-lutidine") from acetone and formaldehyde; the synthesis of 2,4,6-trimethylpyridine ("sym-collidine") from acetone alone or with acetaldehyde; the synthesis of pyridine and beta-picoline from acrolein alone or with acetaldehyde; the synthesis of 3,5-dimethylpyridine from propionaldehyde and formaldehyde; and the synthesis of beta-picoline from acetaldehyde, formaldehyde and propionaldehyde. Many others are known and reported or practiced in the art, and are equally considered within the scope of the description and invention herein.

The catalysts used in these pyridine base synthesis reactions have varied from alumina which was used early-on either alone or as a support for zinc fluoride or other metal salts to an amorphous structure incorporating both silica and alumina which became an important commercial catalyst. See U.S. Pat. Nos. 2,807,618 and 2,744,904; and German Patent No. 1,255,661. Similarly, the reactor designs for these heterogeneous gas-phase reactions have varied within the basic categories of fixed-bed and fluid-bed forms. The advantages of fluidized beds were recognized early-on (see U.S. Pat. No. 2,807,618) as evidenced by the fact that the handful of commercial-scale base synthesis units operating today worldwide all incorporate fluidized catalyst beds. One reason for this is that base synthesis reactions always produce deposits of dark, mostly carbonaceous materials referred to as "coke" which tend to foul the catalyst thereby gradually reducing its activity. Although variations are observed, all catalysts accumulate these coke deposits at a appreciable rate such that periodic action is required. As discarding catalyst is not desirable for economic reasons, regeneration by heating in air or other oxygen-containing gases is commonly employed. This regeneration/combustion process is very exothermic and also best carried out in a fluid bed Process. C. L. Thomas, "Catalytic Processes and Proven Catalysts", Academic Press. N.Y., pp. 11–14 (1970).

Accordingly, a common technique has long been to run two fluid beds concurrently, one for reaction and one for regeneration,. with catalyst continuously or intermittently cycled between the beds. Operating parameters such as circulation rates, contact times, temperatures and the like are readily determined by skilled operators in view of the specific reactions and/or ingredients used. See, e.g., German Patent No. 2,203,384. An ancillary benefit of this technique is that product yields from base synthesis reactions carried out in fluidized beds are recognized to be generally higher than in corresponding fixed-bed reactions. This was emphasized in two families of patents issued to BP Chemicals U.K. Ltd. of London, England, one for alpha-gamma synthesis (British Patent No. 1,188,891; German Patent 1,903,879; and Canadian Patent No. 852 745) and the other for pyridine-beta synthesis (British Patent No. 1,235,390; Canadian Patent No. 851,727; and German Patent No. 1,903,878). These BP patents, and German Patent No. 1,903,878 in particular, compare fixed- and fluid-bed reactions using catalysts of amorphous silica-alumina or metal compounds such as the oxides or fluorides of lead, zinc and cadmium on amorphous silica-alumina supports.

This same advantage of fluid-bed usage was reported by Feitler et al. in U.S. Pat. No. 4,675,410 for base synthesis catalysts composed of shape-selective aluminosilicates (commonly referred to as "zeolites") used in their acidic form. These crystalline zeolites had earlier been reported for base synthesis reactions by Chang et al. in U.S. Pat. No. 4,220,783 both in their acid- or H-form and as ion-exchanged with cadmium, copper or nickel. Several examples in the Chang patent demonstrated deactivation of the catalyst over time thereby also suggesting the desirability of a fluid-bed to reactivate the catalyst by heating in air in any commercial application.

In general, these base synthesis reactions have received universal acceptance as evidenced by their continuous commercial use for many years. The products of base synthesis, including pyridine, alpha-, beta- and gamma-picoline, nearly all the lutidines, and primarily the symmetrical isomer of collidine, have all shown commercial importance in the world chemical market albeit of varying values and volume requirements. See Goe, "Pyridine and Pyridine Derivatives," Encyclopedia of Chemical Technology, Vol. 19, 3rd. Ed. (1982). It is also the case that improvement in the yields of these reactions and variation in their product ratios may be desirable according to market trends for such pyridine-derivative products as the herbicide paraquat, vitamins such as niacin and niacinamide, tire cord adhesive derived from 2-vinylpyridine, the tuberculosis drug Isoniazid, and so forth. One approach to this end has examined variations in reaction conditions such as temperature, velocity or contact time, mole ratios of feed stocks, and the like. Here, optimization of yield or product ratio is generally accomplished by known techniques employed by those skilled in this area. A second approach has involved catalyst variation in which far less predictability exists.

For example, while work early-on was with amorphous silica-alumina or other catalysts, the concentration in recent years has shifted to these so-called shape-selective zeolites which are aluminosilicates of definite crystal structure having activities and pores of size similar to that of other commercially-interesting molecules. See, e.g., E. G. Derouane. "New Aspects of Molecular Shape-Selectivity: Catalysis by Zeolite ZSM-5", *Catalysis by Zeolites,* ed. B. Imelik et al., Elsevier, Amsterdam, pp. 5–18 (1980). These materials are often defined by a constraint index which is an experimentally-derived number based on the observed relative rates of reaction of straight and branched-chain molecules.

Frillette et al., *J. Catal.*, 67, 218 (1981). The term "zeolite" has even acquired a broader meaning in the art, and is accordingly used in this application to mean more than the original crystalline aluminosilicate materials. For example, "zeolite" is understood and meant to also include compositions such as gallosilicates, ferrosilicates, chromosilicates and borosilicates. Crystalline aluminum phosphates ("ALPO's") and silicon-aluminum phosphates ("SALPO's") are also included in its coverage because of their catalytic ability, as is even theoretically-pure crystalline silicalite such as a S-115 material marketed by Union Carbide Corporation of N.Y.

In these zeolite materials, some ion-exchange properties are generally thought to exist due to positive ions associated with the trivalent molecular centers (e.g., aluminum, boron. gallium, etc.) that are present in the network of tetravalent silicon centers. Although ALPO is an exception to this, and silicalite may be an exception but for residual aluminum in its crystal structure, it has also been thought that catalytic activity is associated somehow with these ion-exchange sites. As synthesized, zeolites typically have sodium or quaternary ammonium ions in their crystal structures. If these ions are exchanged for ammonium ($NH_4+$) ions and the resulting ammonium zeolite heated, an acidic or "H-form" zeolite results with these acid centers believed to be associated with some catalytic activity. For instance, an H-form of ZSM-5 zeolite is marketed by The Mobil Corporation of N.Y. and is used in the synthesis of gasoline from methanol.

One approach at optimizing yield and/or product ratios from base synthesis reactions has been to stress maximizing these acidic sites. For example, the Feitler patent claims the specific benefit of a higher ratio of pyridine in the pyridine-beta synthesis by use of a zeolite catalyst of preferably 80–100% this H-form although no direct comparison with other ion-exchanged zeolites is reported.

Other positive ions have also been exchanged for the sodium, ammonium or H-sites in the zeolite structure. For example, cracking catalysts have used a rare earth ion-exchanged form of the large-pore zeolite Y (called "REY"). C. L. Thomas, "Catalytic Processes and Proven Catalysts", *supra*, pp. 30–31. Precious metals have been exchanged in both large-pore and shape-selective zeolites to produce reforming catalysts. E.G. Derouane, "New Aspects of Molecular Shape-Selectivity: Catalysis by Zeolite ZSM-5", *supra*, p. 17. The Chang patent also reported use of zeolites ion-exchanged with cadmium, copper or nickel ions in addition to the H-form of Mobil's ZSM-5 material in base synthesis reactions. The Chang patent did test the catalytic activity of these metal ion-forms, but did not speculate on whether they existed solely or survived in their ionic state or were reduced to base metals.

More recently, Shimizu et al. described base synthesis reactions using shape-selective zeolites treated with thallium, lead or cobalt ions or compounds in an European application, Serial No. 232,182 published Aug. 12, 1987. These metals were ion-exchanged into a zeolite of alkali, ammonium or acid form in an aqueous medium or were mixed in the solid state with no apparent effect from the mode of mixing used. As the Feitler patent, Shimizu also reported the desire for a low yield of beta-picoline from pyridine-beta base synthesis. However, this work does not permit direct comparison with Feitler as Shimizu used a reaction mixture with so little formaldehyde (0.5 moles per mole of acetaldehyde) that it necessarily produced about equal amounts of beta- and gamma-picoline which are of questionable commercial utility. See, e.g., Beschke, *Ullmann Encyclopedia*, p. 593 (1980).

It is in the light of this background, and of the large body of general chemical literature concerned with base synthesis processes (see F. Brody and P. R. Ruby. *Pyridine and Its Derivatives*, E. Klingsberg ed., Vol. 1 (1960); N. S. Boodman et al., *Ibid*, Supplement Abramovitch ed., Vol. 1 (1975); T. D. Bailey, G. L. Goe and E. F. V. Scriven, *Ibid*. Supplement G. R. Newkome ed., Vol. 5 (1984)), that the applicants approached this study with the objectives of providing at least equivalent overall yields and, where appropriate, the selectivity to vary product ratios within reason to meet varying economic conditions.

SUMMARY OF THE INVENTION

The present invention meets these goals through the discovery that shape-selective zeolite materials can be advantageously modified with compounds of tungsten, zinc or tin to produce catalysts that give improved and selective product yields. This is done without the drastic reduction of beta-picoline observed and desired by the Feitler and Shimizu references in the pyridine-beta reaction. Equivalent or improved yields are also achieved in other base synthesis reactions such as the alpha-gamma synthesis in which a high ratio of alpha picoline is obtained without simply decreasing the yield of gamma-picoline from the reaction.

Other aspects of the discovery are that these modified zeolite catalysts differ substantially from those previously taught or suggested in the art as being preferred. For example, contrary to the Feitler Patent, minimal to no acid sites are preferred in the zeolite structure as modified. Although the Feitler, Chang and Shimizu references disclose a wide range of silica-to-alumina ratios, a high-end ratio and therefore lower fraction of ion-exchangeable alumina or other sites are preferred here in the original zeolite structure to be modified. This reduces the sites available for acidic species which may also reduce the concentration of tungsten, zinc or tin needed to be taken up through ion-exchange or otherwise in the treated catalyst to achieve the beneficial effects characteristic of this invention.

The invention further avoids the practical problems encountered with the metal ions taught by the Chang and Shimizu references for use in ion-exchange. Of the six ions mentioned, for example, thallium compounds are extremely toxic and pose severe health hazards as the fluid-bed reactors often used for base synthesis require finely powdered catalysts, some of which inevitably escapes from the system regardless of the care taken. Lead and cadmium compounds are not quite so acutely toxic, but chronic exposure particularly to lead is known to cause severe problems in children. The problem is aggravated in a plant operation where some escape is expected. Nickel and its compounds, on the other hand, are suspected carcinogens and cobalt is a heavy metal known to be environmentally undesirable. Copper compounds, although comparatively innocuous, are known to be toxic and to present waste disposal problems. See, e.g., C. A. Owen, *Copper Deficiency and Toxicity*, pp. 116–120 (1981) and D. C. H. McBrien, "Anaerobic Potentiation of Copper Toxicity and Some Environmental Considerations", *Biological Roles of Copper*. pp. 301–313 (1980).

Such concerns for environmental and human safety are paramount objectives and benefits of the invention along with the surprising catalytic effectiveness and selectivity that has been observed. In this regard, very desirable and unexpected results have been achieved for these base synthesis reactions as described above by the use of the applicants' modified zeolite catalysts.

Related objects and variations as to the detailed aspects of the invention will become apparent from the following description of the preferred embodiment.

DESCRIPTION OF THE PREFERRED EMBODIMENT

For the purposes of promoting an understanding of the principles of the invention, reference will now be made to certain embodiments and specific language will be used to describe the same. It will nevertheless be understood that no limitation of the scope of the invention is thereby intended, such alterations and further modifications of these embodiments, and such further applications of the principles of the invention as described herein being contemplated as would normally occur to one skilled in the art to which the invention relates.

As already stated, one embodiment of the invention is the discovery of an improved catalyst and base synthesis process for the preparation of pyridine or its alkylpyridine derivatives involving the catalytic reaction of one or more aldehydes and/or ketones containing from one to about five carbon atoms, with at least one reactant having more than one carbon atom, with ammonia in the gas phase. The improved catalyst comprises an effective amount of a shape-selective zeolite, as broadly defined above, which has been modified by treatment with one or more metal ions or compounds from the group of consisting of tungsten, zinc or tin. The preferred zeolite has a constraint index of about 1 to 12 and a high silica content and correspondingly low concentration of ion-exchange sites with minimal to no acidic sites present.

The reactants and their ratios used in the invention will vary significantly according to many factors, not the least of which is the base synthesis process under study and the particular pyridine or alkylpyridine base product yield or ratio sought to be achieved. Suitable combinations of reactants include those set forth above and in the Examples below as well as many others known to those skilled in this art. For example, listings and tables of such common reactants and product yields having known commercial importance appear in the Feitler patent (U.S. Pat. No. 4,675,410) and the published Shimizu application (Serial No. EP 232,182), both of which are incorporated herein by reference as to all relevant and material subject matter contained therein. It is understood that all such base synthesis processes and reactant and product combinations are suitable and within the scope of the invention.

Similarly, the reaction conditions such as the molar amounts, temperatures and times used and the appropriate equipment and procedures such as the desirability of pre-mixing or of operating in an inert environment will likewise vary and are well within the skill and knowledge of those practiced in this area. Accordingly, the same require no further elaboration in this specification except as contained in the Examples below, it being understood that such variations are also within the scope of the invention.

Preparation of the modified catalysts in accordance with the invention first involves selection of a shape-selective zeolite material. Many suitable zeolites are known and are commercially available for this purpose. As already stated, one preference is that the zeolite which comprises a crystalline aluminosilicate or other substituted-silicate material have a constraint index of about 1 to 12. Such values are known for many commercial zeolites (see, e.g., the Feitler and Shimizu disclosures incorporated herein by reference) and are otherwise easily calculated by known methods. Frillette et al., *J. Catalysis,* vol. 67, 218–222 (1981).

Other preferences are that the selected zeolite have a relatively low concentration of ion-exchange sites in its structure and that minimal-to-no acidic sites be present after treatment. The first of these is characteristic of a zeolite having a high atomic amount or ratio of silica to the alumina or other substituted-metal ion in its structure. Whereas a silica ratio of 12 to 1,000 is taught by the Feitler and Shimizu disclosures, the preference in this invention is for a ratio in excess of about 100, with the Union Carbide S-115 silicalite material being preferred from work to date. This ratio for S-115 is reported in the Feitler patent to be 350, although available literature from Union Carbide states only that the material is over 99% pure $SiO_2$. Silica ratios approaching about 1,000 or more are acceptable, with the desired result being a high concentration of silica in the zeolite structure with minimal-to-no alumina or other sites susceptible of ion-exchange.

This second preference directly contradicts the Feitler teaching of maximizing the acidic form of the finished zeolite catalyst. The improved catalyst and process of this invention have surprisingly resulted in effective catalytic activity and unexpected product yields and selectivity of various bases by minimizing this same acidic form. In this regard, such use of the term "minimal" or its likeness in this application is meant to define a modified zeolite catalyst having less than 10% of the sites which are available for ion-exchange in fact occupied by hydrogen ions or other acidic species as described in the Feitler patent. A very low alumina-content zeolite is thus preferred, such as the S-115 silicalite material from Union Carbide with only trace amounts of alumina or other such metal ions present in its crystal structure.

Once a zeolite is selected, an improved catalyst is made in accordance with the invention by effectively modifying the zeolite material through treatment with one or more of the preferred metal ions of tungsten, zinc or tin or compounds containing the same. This treatment may be carried out in any number of ways known in the art and may be carried out several times if desired to ensure substantial metal uptake on the zeolite.

For example, a preferred method of treatment is to add the zeolite to an aqueous solution of the desired tungsten, zinc or tin compound in stoichiometric excess and then to heat the mixture for some time at a predetermined temperature accompanied by stirring. The metal compounds used are soluble salts such as ammonium tungstate in the case of tungsten and nitrates, halides or acetates in the case of zinc or tin. This is followed by filtering, rinsing and drying, and then calcining at elevated temperature to obtain the finished catalyst. An alternate or possible further procedure is to prepare a physical mixture of the zeolite and the desired metal salt either dry or in the presence of enough water to constitute a paste or similar consistency, and then to complete the modification by blending or other suitable physical means. These and other similar procedures known in the art are all within the scope of the invention.

As a result of this treatment procedure, an effective amount of the tungsten, zinc or tin metal is taken up in the zeolite structure thereby modifying it to produce the improved catalyst in accordance with the invention. The amount and method of this uptake will vary depending on many factors such as the identity and concentration of reactants, the specific treatment procedures and the like, all of which are within the skill of those experienced in this area to select and to control. For example, no minimum or threshhold level of metal uptake is required with all amounts expected to produce some improved catalytic activity or effectiveness in later use. The same are therefore within the scope of the invention so long as the characteristics described herein are met. Nevertheless, concentrations up to about 1.0 mg equivalent/g of the selected metal in the modified catalyst are obtainable and may be desired in a given circumstance.

Similarly, no particular method of uptake is required with physical absorption, adsorption and other forces coming into play and with chemical means such as ion-exchange and the like also occurring with given reactants exposed to certain treatment procedures. With zinc and tin, for example, an added benefit is that any available or existing acidic sites in the zeolite are believed to be substantially ion-exchanged with the preferred metal during the treatment procedure thereby minimizing these acidic sites as preferred in accordance with the invention. The same may also be an aspect of or involved in the uptake of tungsten as well, but its mechanism of modifying and affecting the zeolite whether physical or chemical or both is less clear from testing performed thus far.

In any case, the treatment procedure may occur before or after the zeolite is formulated into a catalyst matrix or binder. In this regard, pure zeolites are commonly in the form of very fine powders suitable neither for fixed- or fluid-bed usage. To be useful, the zeolite powders are typically incorporated into a binder or matrix and then pelletized or extruded (With a fixed-bed catalyst) or ground or spray-dried (with a fluid-bed catalyst) to produce a form having commercial application. The applicants' improved base synthesis process may be operated in a fixed- or a fluid-bed reactor to achieve the overall effective yields and selective product ratios characteristic of the invention. Nevertheless, a fluid-bed reactor and catalyst are preferred in order to also achieve the expected higher yields and ease of regeneration and use characteristic of such systems. The equipment set up and operation of fluid-bed reactors vary according to many factors tied to the particular reaction under consideration. The same are readily constructed by those of ordinary skill in the art, and are all within the scope of the invention herein. Reaction parameters such as temperature, feed mole ratios, feed velocity and contact time and the like vary over a wide range of operable conditions also well known and within the scope of the invention.

As previously discussed, many base synthesis processes are known and are also within the scope of the invention herein. In addition to the specific Examples below and to the disclosures incorporated by reference above, for the pyridine-beta synthesis it is generally preferred that a feed of formaldehyde to acetaldehyde in a mole ratio of at least about 1:1 is used. The addition of methanol to the extent of about 5 to 70% of the formaldehyde component is also preferred, as originally described in U.S. Pat. No. 2,807,618. At least a portion of the formaldehyde can further be replaced by para-formaldehyde or sym-trioxane, and water can be present as desired to provide a stable, storable solution. Ammonia is supplied in a ratio of at least about 0.6:1 to the total organic components in the feed, with a range of about 0.7 to 1.5 being more preferred and about 0.8 to 1.2 being most preferred from testing to date. The feed rate is in turn chosen to give good fluidization of the bed, usually in the range of a superficial velocity between about 0.3 to 4.0 ft./sec. Temperature of the reaction is preferably between about 350° C. and 550° C. more preferably between about 400° C. and 500° C. and most preferably at about 450° C. The products of the reaction, being pyridine and beta-picoline, are condensed and separated into pure compounds by drying and distillation as is well known in the art. By way of a second example, the alpha-gamma reaction is preferably carried out in much the same way except that formaldehyde and methanol are left out of the feed mixture.

While the invention has been described in detail in the foregoing description, the same is to be considered as illustrative and not restrictive in character, it being understood that only the preferred embodiments have been described and that all changes and modifications that come within the spirit of the invention are desired to be protected. In the same regard, the following specific Examples are given in further explanation and description of these embodiments and are meant to be exemplary and not limitations thereof.

EXAMPLE 1

Modified Catalyst Preparation and Use

Several modified zeolite catalysts in accordance with the invention were prepared using representative procedures well known in the art, there being other known techniques equally suitable and within the scope of the invention. In the Examples below, this involved use of a S-115 silicalite powder obtained from Union Carbide which had been already formulated into a silica-alumina matrix at a 25% weight concentration and spray-dried to an appropriate particulate size and configuration for use in a fluidized-bed reactor. An alternative was to directly treat this S-115 powder with one or more of the preferred tungsten, zinc or tin compounds, followed by mixing this modified zeolite with wet kaolin powder which was later dried and calcined to form an appropriate catalyst for fluid-bed usage.

In either case, one method of treatment involved heating the formulated silicalite catalyst or unformulated powder at temperatures in the range of about 70°–100° C. with stirring in an aqueous solution containing a stoichiometric excess of the selected metal compound. Stirring was continued for at least 2 hours to assure substantial modification of the catalyst in accordance with the invention, and was followed by filtering, rinsing thoroughly with water, drying and calcining the catalyst at about 500° C. or above before subsequent use. A second alternate or additional procedure involved mixing the formulated or unformulated silicalite with the selected metal compound in a paste-like consistency to permit modification, followed by drying and calcining as before.

One base synthesis process used to test these modified zeolite catalysts was the pyridine-beta synthesis. The reaction was conducted in an externally gas-heated fluid-bed reactor of standard design having a 1.6 inch internal diameter and containing 750 mL of catalyst. The temperature of the catalyst bed was maintained at 450° C. The organic feed into the reactor comprised acetaldehyde and formaldehyde in a 1:1 mole ratio, with the formaldehyde being a mixture containing 45% formaldehyde, 10% methanol and the remainder water. Ammonia was also fed into the reactor at a mole ratio of 1.2 compared to the total organic feed. This organic feed was injected directly above the distributor plate, while ammonia was introduced below the distributor plate according to common and known procedures. The products exiting the top of the reactor were captured and condensed. Methanol was added to homogenize the product mixture which was then analyzed using standard gas chromatography techniques.

A second base synthesis reaction also tested was the alpha-gamma synthesis. This reaction was conducted similar to the procedure for pyridine-beta synthesis except that the organic feed contained only acetaldehyde. The overall yield and product mix was again determined by gas chromatographic analysis as reported in the specific Examples below.

EXAMPLE 2

Tungsten-modified zeolite catalyst was prepared according to the procedures of Example 1 by first wetting 62.5 g (0.25 mol) of $H_2WO_4$ with 40 mL of water. This wet mixture was then heated with 400 mL of concentrated ammonium hydroxide for a few minutes at about 50° C., and the solution was diluted to 2.5 L with water. 1 Kg of 25% S-115 catalyst in a silica-alumina matrix was then added and the mixture stirred for 2 hours at about 80° C. The mixture was filtered, rinsed with four 2.5 L amounts of water, and was dried overnight in a wide pan. The modified catalyst was then calcined for 4 hours at 500° C., during which significant tungsten uptake was confirmed by the characteristic pale yellow appearance of the catalyst. An appropriate amount of this tungsten modified zeolite catalyst was then used in the pyridine-beta synthesis reaction as described in Example 1, with the product mixture containing 32 weight percent pyridine and 16 weight percent beta-picoline compared to the total organic feed stream passed through the reactor. The amount of alpha-picoline also detected was 1 weight percent.

EXAMPLE 3

Zinc-modified zeolite catalyst was prepared in accordance with the procedure of Example 1 by dissolving 74.4 g (0.25 mol) of $Zn(NO_3)_2 \cdot 6H_2O$ in water and diluting this solution to 2.5 L with additional water. 1 Kg of 25% S-115 catalyst formulated in a silica-alumina matrix was then added and the mixture heated and stirred for 2 hours at about 80° C. The mixture was filtered and rinsed with four 2.5 L equivalents of water. The modified catalyst was dried overnight in a wide pan and calcined for four hours at 500° C. Significant zinc uptake on the catalyst, and a corresponding and desired decrease in acidic sites to minimal levels, was confirmed by acid leaching of the catalyst making the leachate basic and subsequent precipitation with hydrogen sulfide. Use of this zinc-modified zeolite catalyst in the pyridine-beta synthesis reaction described in Example 1 yielded product containing 34 weight percent pyridine, 14 weight percent beta-picoline and 1 weight percent of alpha-picoline compared to the total organic feed stream passed through the reactor. Use of this same catalyst in the alpha-gamma synthesis reaction also of Example 1 gave a product containing 16 weight percent alpha-picoline and 14 weight percent gamma-picoline with 3 weight percent pyridine.

EXAMPLE 4

Tin-modified zeolite catalyst was prepared in accordance with the procedure of Example 1 by dissolving 74.4 g (0.25 mol) of stannous chlor in a solution of 1.5 L water and 0.5 L concentrated nitric acid, and diluting this solution to 2.5 L with additional water. 1 Kg of 25% S-115 catalyst formulated in a silica-alumina matrix was then added and the mixture heated and stirred for two hours at about 80° C. The mixture was filtered, rinsed with four 2.5 L equivalents of water. The modified catalyst was dried overnight in a wide pan and calcined for 4 hours at 500° C. Significant tin uptake on the catalyst, and a corresponding and desired decrease in acidic sites to minimal levels, was confirmed by fusing an amount of catalyst with KOH and then dissolving this in water and precipitating with sodium sulfide. Use of this tin-modified zeolite catalyst in the pyridine-beta synthesis reaction described in Example 1 yielded product containing 34 weight percent pyridine, 14 weight percent beta-picoline and 1 weight percent of alpha-picoline compared to the total organic feed stream passed through the reactor. Use of this same catalyst in the alpha-gamma synthesis reaction also of Example 1 gave a product containing 23 weight percent alpha-picoline and 15 weight percent gamma-picoline with 2 weight percent pyridine.

EXAMPLE 5

Zinc-tungsten modified catalyst was prepared in accordance with the procedure of Example 1 by adding 1 Kg of 25% S-115 formulated in a silica-aluminum matrix to a 2.5 L aqueous solution which already contained 74.4 g (0.25 mol.) $Zn(NO_3)_2 \cdot 6H_2O$. The mixture was stirred for 2 hours at about 80° C., and the catalyst filtered and rinsed with four 2.5 L amounts of water followed by drying for about 18 hours at 120° C. A second solution was then prepared by wetting 62.5 g (0.25 mol) of $H_2WO_4$ with 40 mL of water. 400 mL of concentrated ammonium hydroxide was then added and the mixture stirred at about 50° C. until the $H_2WO_4$ dissolved. The solution was then diluted to 2.5 L with additional water. The dried zinc-modified zeolite catalyst was then added to this second solution and the mixture stirred for 2 hours at about 80° C. The mixture was filtered and the catalyst was once again rinsed with four 2.5 L portions of water, dried overnight in a wide pan, and calcined for 4 hours at 500° C. Confirmation of the significant tungsten uptake was once again made by the characteristic pale yellow appearance of the catalyst, and confirmation of zinc uptake was by acid leaching of the catalyst making the leachate basic and subsequent precipitation with hydrogen sulfide as in Example 3. Subsequent use of this zinc-tungsten modified catalyst in the pyridine-beta synthesis reaction of Example 1 gave a product containing 34 weight percent pyridine and 16 weight percent beta-picoline with 1 weight percent alpha-picoline being present compared to the total organic feed stream passed through the reactor. These results, as with all the Examples above, were significant yields both of the overall reaction and of individual components which have established and valuable commercial uses around the world.

What is claimed is:

1. A base synthesis process for the preparation of pyridine or its alkylpyridine derivatives in high yield comprising reacting a $C_2$ to $C_5$ aldehyde, a $C_3$ to $C_5$ ketone or a mixture thereof, with ammonia and, optionally, formaldehyde, in the gas phase and in the presence of an effective amount of a modified zeolite catalyst having a constraint index of about 1 to 12 which has been treated with one or more ions of or compounds containing tungsten, zinc or tin.

2. The process of claim 1 in which the organic reactants are acetaldehyde and formaldehyde, and comprising the additional step of recovering pyridine and beta-picoline as the products of said reacting.

3. The process of claim 2 in which the reactants also include methanol.

4. The process of claim 2 in which the formaldehyde is in the form of paraformaldehyde or sym-trioxane.

5. The process of claim 1 in which the reactant is acetaldehyde, and additionally comprising recovering alpha- and gamma-picoline as the products of said reacting.

6. The process of claim 1 in which the zeolite is ZSM-5.

7. The process of claim 1 in which the zeolite is silicalite.

8. The process of claim 1 in which the zeolite has been treated with a compound of zinc.

9. The process of claim 8 in which the compound of zinc is zinc nitrate.

10. The process of claim 8 in which the compound of zinc is zinc chloride.

11. The process of claim 1 additionally comprising formulating the zeolite into a binder containing silica and alumina for use in a fluid-bed reactor.

12. The process of claim 1 in which the reactants are a mixture of acetaldehyde, formaldehyde and propionaldehyde, and additionally comprising recovering pyridine and beta-picoline as the products of said reacting.

13. The process of claim 1 in which the zeolite has been treated with a compound of tin.

14. The process of claim 1 in which the zeolite has been treated with a compound of tungsten.

15. The process of claim 14 in which the compound of tungsten is ammonium tungstate.

* * * * *